(12) United States Patent
Crawford

(10) Patent No.: US 11,478,645 B2
(45) Date of Patent: Oct. 25, 2022

(54) SYSTEM AND METHOD FOR CONTROLLING NEUROSTIMULATION ACCORDING TO USER ACTIVITY AND AUTOMATED BALANCING OF STIMULATION PROGRAM DURATION

(71) Applicant: ADVANCED NEUROMODULATION SYSTEMS INC., Plano, TX (US)

(72) Inventor: Christopher S. L. Crawford, Sunnyvale, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 17/139,961

(22) Filed: Dec. 31, 2020

(65) Prior Publication Data

US 2022/0203097 A1 Jun. 30, 2022

(51) Int. Cl.
*A61N 1/36* (2006.01)
*A61N 1/372* (2006.01)

(52) U.S. Cl.
CPC ..... *A61N 1/36139* (2013.01); *A61N 1/36067* (2013.01); *A61N 1/36071* (2013.01); *A61N 1/36114* (2013.01); *A61N 1/37217* (2013.01)

(58) Field of Classification Search
CPC ......................... A61N 1/36139; A61N 1/36067
USPC .......................................................... 607/46
See application file for complete search history.

(56) References Cited

U.S. PATENT DOCUMENTS

| | | | |
|---|---|---|---|
| 7,212,110 B1 | 5/2007 | Martin et al. | |
| 7,228,179 B2 | 6/2007 | Campen et al. | |
| 7,571,007 B2 | 8/2009 | Erickson et al. | |
| 8,224,453 B2 | 7/2012 | De Ridder | |
| 8,682,441 B2 | 3/2014 | De Ridder | |
| 10,124,177 B2 | 11/2018 | Kumar | |
| 10,314,550 B2 | 6/2019 | Frieder et al. | |
| 10,602,964 B2 | 3/2020 | Kerber | |
| 10,786,676 B2 | 9/2020 | Molnar et al. | |
| 2004/0088374 A1 | 5/2004 | Webb et al. | |
| 2005/0043652 A1 | 2/2005 | Lovett et al. | |
| 2006/0170486 A1 | 8/2006 | Tranchina et al. | |
| 2010/0010584 A1 | 1/2010 | Skelton et al. | |

(Continued)

FOREIGN PATENT DOCUMENTS

WO WO-2001/093953 A1 12/2001
WO WO-2011085228 A1 7/2011

(Continued)

OTHER PUBLICATIONS

Das, L. B. et al., "Determination of Microlocation Using the BLE Protocol, and Wireless Sensor Networks," 2018 IEEE 3rd International Conference on Computing, Communication and Security (ICCCS), Kathmandu, 2018, pp. 64-69; 6 pages.

(Continued)

*Primary Examiner* — Nadia A Mahmood

(74) *Attorney, Agent, or Firm* — Norton Rose Fulbright US LLP

(57) ABSTRACT

This application is generally related to systems and methods for providing a medical therapy to a patient by tracking patient activity and adjusting medical therapy based on occurrence of different types of activities performed by the patient while automatically balancing stimulation program duration.

19 Claims, 10 Drawing Sheets

(56) References Cited

U.S. PATENT DOCUMENTS

| | | | |
|---|---|---|---|
| 2010/0100148 A1* | 4/2010 | Min | A61N 1/3712 607/27 |
| 2010/0280440 A1 | 11/2010 | Skelton et al. | |
| 2011/0172738 A1 | 7/2011 | Davis et al. | |
| 2014/0135592 A1 | 5/2014 | Ohnemus et al. | |
| 2014/0350966 A1 | 11/2014 | Khatana et al. | |
| 2019/0329051 A1 | 10/2019 | Moffitt et al. | |
| 2020/0303063 A1 | 9/2020 | Sharma et al. | |

FOREIGN PATENT DOCUMENTS

| | | |
|---|---|---|
| WO | WO-2019210117 A1 | 10/2019 |
| WO | WO-2020191299 A1 | 9/2020 |

OTHER PUBLICATIONS

Schu, S. et al. "A Prospective, Randomised, Double-blind, Placebo-controlled Study to Examine the Effectiveness of Burst Spinal Cord Stimulation Patterns for the Treatment of Failed Back Surgery Syndrome," Neuromodulation 2014; 17: 443-450; 8 pages.

Al-Kaisy, A. et al. "Sustained Effectiveness of 10 kHz High-frequency Spinal Cord Stimulation for Patients with Chronic, Low Back Pain: 24-month Results of a Prospective Multicenter Study," Pain Med. Mar. 2014; 15: 347-54, 8 pages.

Patent Cooperation Treaty, International Search Report and Written Opinion issued for PCT Application No. PCT/US2021/065853, dated Apr. 11, 2022, 10 pages.

United States Patent and Trademark Office, Non-Final Office Action issued for U.S. Appl. No. 17/139,967, dated Apr. 26, 2022, and entitled "System and Method for Controlling Neurostimulation According to User Activity Detected Through Patient Use of Icon Driven User Interface," filed Dec. 31, 2020, 16 pages.

* cited by examiner

SYSTEM AND METHOD FOR CONTROLLING NEUROSTIMULATION ACCORDING TO USER ACTIVITY AND AUTOMATED BALANCING OF STIMULATION PROGRAM DURATION

BACKGROUND

Smartphones and smartwatches include a number of components that permit tracking of the activity of users of the devices. For example, smartphones commonly include global positioning system (GPS) components, accelerometers, and other sensors. The components of these have been used to track a number of activities including exercise activities, user sleep patterns, health conditions, driving, and other common user activities. Metrics for these various activities are commonly calculated by one or more applications on these devices and can be provided to the users to help guide their activities and to provide an assessment of the health of the patients.

The FITBIT VERSA SMARTWATCH™, SAMSUNG GALAXY SMARTWATCH™, and APPLE WATCH™ devices are example commercially available devices that include accelerometers, temperature sensors, heart rate monitors, electrocardiogram sensors, blood oxygen saturation sensors, and other sensors to provide users a summary of daily activities and overall analysis of the activities.

More advanced tracking of specific disorders has begun using commercially available devices. For example, APPLE has developed a "MOVEMENT DISORDER" application programming interface (API) to allow monitoring of movement disorder symptoms. The software collects data from the APPLE WATCH™ of a patient and analyzes the movement data to detect and quantify common symptoms of Parkinson's Disease (PD). The relevant symptoms include tremors, indicated by shaking and quivering and dyskinesia (a side-effect of pharmacological treatments of PD that causes fidgeting and swaying motions in patients).

Additionally, U.S. Pat. No. 10,314,550 describes using smartphones and/or smartwatch type devices to monitor for possible mental or physical health concerns. The patient tracking in the '550 patent automatically learns user activity patterns and detects significant deviations therefrom. The deviations are automatically analyzed for known correlations to mental or physical concerns. The deviations may be provided to medical professionals to assist provisional of medical care to the patient or to caretakers responsible for the respective patients.

Neurostimulation systems are systems that apply electrical stimulation to one or more targets of a patient's neural tissues to treat neurological disorders or other disorders of patients. It has been proposed to use external devices (such as "fitness tracking" devices) to track patient response to neurostimulation to determine whether the neurostimulation therapy is achieving an improvement in patient condition and/or quality of life. Although fitness tracking and smartwatches have been suggested to augment conventional patient controller devices for neurostimulation systems, many proposed designs merely augment conventional external patient controller devices rather than provide new neurostimulation system capabilities.

SUMMARY

In some embodiments, systems and methods provide neurostimulation to a patient by monitoring activities of the patient using at least one external device. Activities of the patient are monitored and detected using one or more sensors of an implantable device or an external device. The sensors may include sensors for sensing physiological conditions, sensors for detection movement or location, and/or any other suitable sensors. In some embodiments, an activity profile for the patient is determined that represents expected times when the patient will engage in a plurality of different activities of the patient.

In some embodiments, patient activity is detected using location determining circuitry and location-based algorithms to correlate location to activity. Microlocation processing algorithms may be employed to determine patient activity within the patient's domicile as one example. The monitoring of activities of a patient may include repetitively detecting a location of the patient using location determining circuitry of the external device of the patient. The circuitry for location-based activity tracking may including cellular communication circuitry, WiFi circuitry, and Bluetooth circuitry. Location-based activity detection may include detecting an amount of time spent at an identified location.

In some embodiments, monitoring activities of the patient may comprise obtaining data pertaining to physiological signals of the patient using a wearable device or an implanted device. The physiological signals may include heart rate data, electrocardiogram data, a sleep quality data, body temperature data, blood oxygen saturation data, and blood glucose data.

In some embodiments, the neurostimulation system includes an external controller that receives user input from the patient by the external controller that is indicative of patient activities being performed by the patient. The patient may provide user input by selecting respective ones of activity icons displayed on or more user interface screens where each respective icon represents a distinct patient activity. The user interface screen(s) may receive input from the user indicative of ease or difficulty for the patient in performing a respective activity. Also, the user interface(s) may receive input from the user indicative of a level of pain experienced by the patient at a respective point in time.

In some embodiments, a patient activity profile is generated from the activity data collected from the implanted and/or external devices of the patient. In some embodiments, the patient activity data is communicated to a remote care management system, wherein the remote care management system determines the activity profile for the patient. The remote care management system may perform an averaging calculation of observed times for patient activities of the activity profile; calculate average start times of respective activities for the activity profile; may calculate average end times of respective activities for the activity profile; apply a calculation of frequency of performance of activities to determine the activity profile; and/or apply an averaging calculation to determine average duration of activities for the activity profile. Such suitable processing of patient activity data into activity metrics may be employed to create a patient activity profile.

The neurostimulation system may store a plurality of different stimulation programs for use by a neurostimulation system of the patient such that each stimulation program is adapted to provide a different stimulation effect on the patient. The different stimulation programs may comprise different stimulation amplitude levels for application of electrical pulses to the patient. The different stimulation programs are adapted to provide a beneficial stimulation therapy specific to the patient. The different stimulation programs may apply electrical pulses at different frequencies. The different stimulation programs may apply electrical pulses to different neural targets. The different stimulation programs may apply electrical pulses using different stimulation patterns. The different stimulation programs may cause different side effects for the patient. One of the different stimulation programs may be adapted to modify blood flow to a region of the patient's body or otherwise modify cardiac activity of the patient. One of the different stimulation programs may adapted to treat pain of the patient or treat a motor disorder symptom of the patient.

The implantable pulse generator of the neurostimulation system is controlled to generate electrical pulses according to ones of the plurality of different stimulation programs with different stimulation effects for application to neural tissue of the patient according to activities of the patient. In some embodiments, stimulation programs are applied according to times defined by at least the activity profile of the patient.

In some embodiments, the neurostimulation system retrieves a stimulation scheduling parameter that defines a percentage or length of time for scheduling an identified stimulation program and dynamically adjusting scheduling of the identified stimulation program based on detected activities of the patient subject to scheduling compliance with the stimulation scheduling parameter.

In some embodiments, a scheduling process of the neurostimulation system detects when the patient engages in an activity outside of times defined in a patient profile and automatically reschedules selection of one or more of the stimulation programs for generation of electrical pulses by the implantable pulse generator. The scheduling process may detect performance of a non-regular activity of the patient that is performed at varied times and switches application of stimulation programs by the implantable pulse generator by detecting performance of the non-regular activity.

The scheduling process may resume a respective stimulation program for a regularly performed activity when the stimulation scheduling process detects an end point of the non-regularly activity of the patient. The scheduling process may detect early performance of an otherwise regularly performed activity and automatically reschedules an end time for a respective stimulation program for the regularly performed activity. The scheduling process may detect termination of an activity represented in the activity profile at a time later than expected and reschedules stimulation for one or more stimulation programs of subsequent activities defined in the activity profile. When the scheduling process detects performance of an activity outside of a time period defined in the activity profile of the patient, the scheduling process may select a stimulation program corresponding to activity being performed outside of a time period defined in the activity profile, and a balancing process modifies timing of application of one or more other stimulation programs to balance performance of stimulation programs according to one or more clinician set parameters.

In some embodiments, the neurostimulation system stores a plurality of clinician defined scheduling rules that define time periods for provision of stimulation according to ones of the plurality of different stimulation programs based on performance of respective activities performed by the patient. A scheduling process of the neurostimulation system controls when an implantable pulse generator of the neurostimulation system generates electrical pulses according to ones of the plurality of different stimulation programs with different stimulation effects for application to neural tissue of the patient according to times defined by at least the activity profile and the scheduling rules.

DETAILED DESCRIPTION

Neurostimulation systems are devices that generate electrical pulses and deliver the pulses to neural tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) which is often used to treat chronic pain such as Failed Back Surgery Syndrome (FBSS) and Complex Regional Pain Syndrome (CRPS). SCS devices may also treat a number of other disorders in addition to chronic pain. Dorsal root ganglion (DRG) stimulation is another example of a neurostimulation therapy in which electrical stimulation is provided to the dorsal root ganglion structure that is just outside of the epidural space. DRG stimulation is also generally used to treat chronic pain but may treat other disorders. Neurostimulation therapies including SCS stimulation and DRG stimulation are also known to effect other physiological processes such as cardiac, respiratory, and digestive processes as examples.

Neurostimulation systems generally include a pulse generator and one or more leads. A stimulation lead includes a lead body of insulative material that encloses wire conductors. The distal end of the stimulation lead includes multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or "can") that encloses circuitry for generating the electrical stimulation pulses, control circuitry, communication circuitry, a rechargeable or primary cell battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Figure 1:
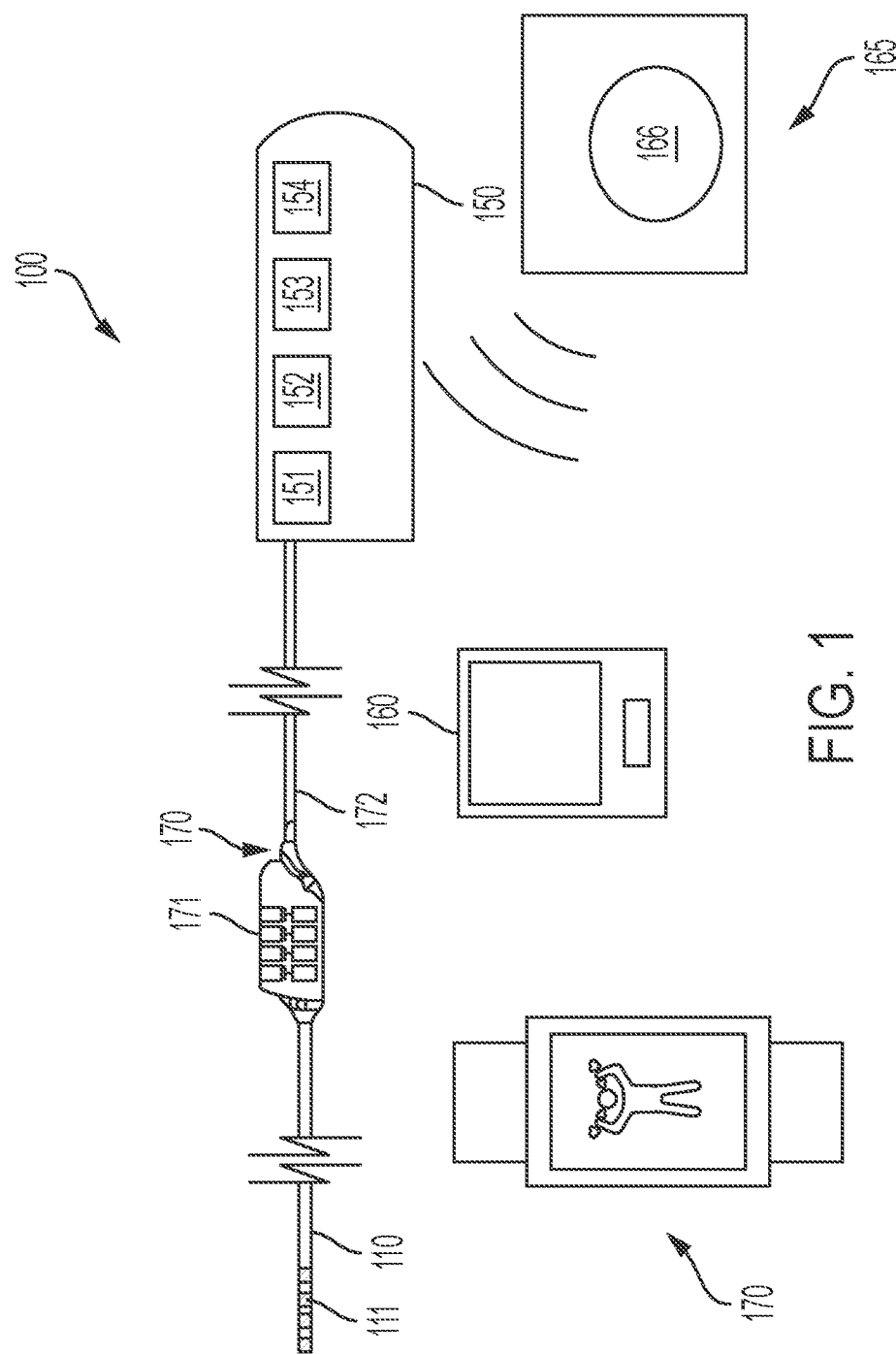
FIG. 1 depicts a neurostimulation system according to some embodiments.

Stimulation system 100 is shown in FIG. 1 according to some embodiments. Stimulation system 100 generates electrical pulses for application to tissue of a patient to treat one or more disorders of the patient. System 100 includes an implantable pulse generator (IPG) 150 that is adapted to generate electrical pulses for application to tissue of a patient. Examples of commercially available implantable pulse generators include the PROCLAIM XR™ and INFINITY™ implantable pulse generators (available from ABBOTT, PLANO Tex.). Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154 (e.g., BLUETOOTH communication circuitry), and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, metal ribbons, traces, lines, or the like (not shown) from the internal circuitry of pulse generator 150 to output connectors (not shown) of pulse generator 150 which are typically contained in the "header" structure of pulse generator 150. Commercially available ring/spring electrical connectors are frequently employed for output connectors of pulse generators (e.g., "Bal-Seal" connectors). The terminals of one or more stimulation leads 110 are inserted within connector portion 171 for electrical connection with respective connectors or directly within the header structure of pulse generator 150. Thereby, the pulses originating from IPG 150 are conducted to electrodes 111 through wires contained within the lead body of lead 110. The electrical pulses are applied to tissue of a patient via electrodes 111.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

External controller device 160 is a device that permits the operations of IPG 150 to be controlled by a user after IPG 150 is implanted within a patient. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. The interface functionality of controller device 160 is implemented using suitable software code for interacting with the user and using the wireless communication capabilities to conduct communications with IPG 150. One or more user interface screens may be provided in software to allow the patient and/or the patient's clinician to control operations of IPG 150 using controller device 160. In some embodiments, commercially available devices such as APPLE iOS devices are adapted for use as controller device 160 by include one or more "apps" that communicate with IPG 150 using, for example, BLUETOOTH communication.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc.

Controller device 160 may permit programming of IPG 150 to provide a number of different stimulation patterns or therapies to the patient as appropriate for a given patient and/or disorder. Examples of different stimulation therapies include conventional tonic stimulation (continuous train of stimulation pulses at a fixed rate), BurstDR stimulation (burst of pulses repeated at a high rate interspersed with quiescent periods with or without duty cycling), "high frequency" stimulation (e.g., a continuous train of stimulation pulses at 10,000 Hz), noise stimulation (series of stimulation pulses with randomized pulse characteristics such as pulse amplitude to achieve a desired frequency domain profile). Any suitable stimulation pattern or combination thereof can be provided by IPG 150 according to some embodiments. Controller device 160 communicates the stimulation parameters and/or a series of pulse characteristics defining the pulse series to be applied to the patient to IPG 150 to generate the desired stimulation therapy.

Examples of suitable therapies include tonic stimulation (in which a fixed frequency pulse train) is generated, burst stimulation (in which bursts of multiple high frequency pulses) are generated which in turn are separated by quiescent periods, "high frequency" stimulation, multi-frequency stimulation, and noise stimulation. Descriptions of respective neurostimulation therapies are provided in the following publications: (1) Schu S., Slotty P. J., Bara G., von Knop M., Edgar D., Vesper J. A Prospective, Randomised, Double-blind, Placebo-controlled Study to Examine the Effectiveness of Burst Spinal Cord Stimulation Patterns for the Treatment of Failed Back Surgery Syndrome. Neuromodulation 2014; 17: 443-450; (2) Al-Kaisy A1, Van Buyten J P, Smet I, Palmisani S, Pang D, Smith T. 2014. Sustained effectiveness of 10 kHz high-frequency spinal cord stimulation for patients with chronic, low back pain: 24-month results of a prospective multicenter study. Pain Med. 2014 March; 15(3):347-54; and (3) Sweet, Badjatiya, Tan D1, Miller. Paresthesia-Free High-Density Spinal Cord Stimulation for Postlaminectomy Syndrome in a Prescreened Population: A Prospective Case Series. Neuromodulation. 2016 April; 19(3):260-7. Noise stimulation is described in U.S. Pat. No. 8,682,441B2. Burst stimulation is described in U.S. Pat. No. 8,224,453 and U.S. Published Application No. 20060095088. A "coordinated reset" pulse pattern is applied to neuronal subpopulation/target sites to desynchronize neural activity in the subpopulations. Coordinated reset stimulation is described, for example, by Peter A. Tass et al in COORDINATED RESET HAS SUSTAINED AFTER EFFECTS IN PARKINSONIAN MONKEYS, Annals of Neurology, Volume 72, Issue 5, pages 816-820, November 2012, which is incorporated herein by reference. The electrical pulses in a coordinated reset pattern are generated in bursts of pulses with respective bursts being applied to tissue of the patient using different electrodes in a time-offset manner. The time-offset is selected such that the phase of the neural-subpopulations are reset in a substantially equidistant phase-offset manner. By resetting neuronal subpopulations in this manner, the population will transition to a desynchronized state by the interconnectivity between the neurons in the overall neuronal population. All of these references are incorporated herein by reference.

For implementation of the components within IMD 14, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION" which is incorporated herein by reference.

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

External charger device 165 may be provided to recharge battery 153 of IPG 150 according to some embodiments when IPG 150 includes a rechargeable battery. External charger device 165 comprises a power source and electrical circuitry (not shown) to drive current through coil 166. The patient places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. In operation during a charging session, external charger device 165 generates an AC-signal to drive current through coil 166 at a suitable frequency. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150. IPG 150 may also communicate status messages to external charging device 165 during charging operations to control charging operations. For example, IPG 150 may communicate the coupling status, charging status, charge completion status, etc.

System 100 may include external wearable device 170 such as a smartwatch or health monitor device. Wearable device may be implemented using commercially available devices such as FITBIT VERSA SMARTWATCH™, SAMSUNG GALAXY SMARTWATCH™, and APPLE WATCH™ devices with one or more apps or appropriate software to interact with IPG 150 and/or controller device 160. In some embodiments, wearable device 170, controller device 160, and IPG 150 conduct communications using BLUETOOTH communications.

Wearable device 170 monitors activities of the patient and/or senses physiological signals. Wearable device 170 may track physical activity and/or patient movement through accelerometers. Wearable device 170 may monitory body temperature, heart rate, electrocardiogram activity, blood oxygen saturation, and/or the like. Wearable device 170 may monitor sleep quality or any other relevant health related activity.

Wearable device 170 may provide one or more user interface screens to permit the patient to control or otherwise interact with IPG 150. For example, the patient may increase or decrease stimulation amplitude, change stimulation programs, turn stimulation on or off, and/or the like using wearable device 170. Also, the patient may check the battery status of other implant status information using wearable device 170.

Wearable device 170 may include one or more interface screens to receive patient input. In some embodiments, wearable device 170 and/or controller device 160 are implemented (individually or in combination) to provide an electronic patient diary function. The patient diary function permits the patient to record on an ongoing basis the health status of the patient and the effectiveness of the therapy for the patient. In some embodiments as discussed herein, wearable device 170 and/or controller device 160 enable the user to indicate the current activity of the patient, the beginning of an activity, the completion of an activity, the ease or quality of patient's experience with a specific activity, the patient's experience of pain, the patient's experience of relief from pain by the stimulation, or any other relevant indication of patient health by the patient.

Figure 2:
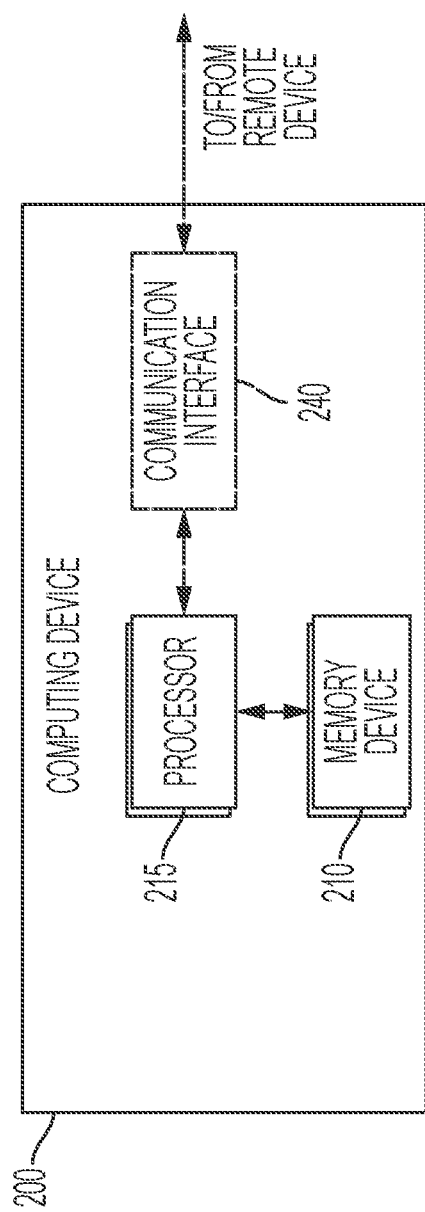
FIG. 2 depicts a computing device that may be included within a neurostimulation system or to communicate with a neurostimulation system according to some embodiments.

FIG. 2 is a block diagram of one embodiment of a computing device 200 that may be used to according to some embodiments. Computing device 200 may be used to implement external controller device 160, wearable device 170, remote care management servers, or other computing system according to some embodiments.

Computing device 200 includes at least one memory device 210 and a processor 215 that is coupled to memory device 210 for executing instructions. In some embodiments, executable instructions are stored in memory device 210. In some embodiments, computing device 200 performs one or more operations described herein by programming processor 215. For example, processor 215 may be programmed by encoding an operation as one or more executable instructions and by providing the executable instructions in memory device 210.

Processor 215 may include one or more processing units (e.g., in a multi-core configuration). Further, processor 215 may be implemented using one or more heterogeneous processor systems in which a main processor is present with secondary processors on a single chip. In another illustrative example, processor 215 may be a symmetric multi-processor system containing multiple processors of the same type. Further, processor 215 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 210 is one or more devices that enable information such as executable instructions and/or other data to be stored and retrieved. Memory device 210 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 210 may be configured to store, without limitation, application source code, application object code, source code portions of interest, object code portions of interest, configuration data, execution events and/or any other type of data.

Computing device 200, in the illustrated embodiment, includes a communication interface 240 coupled to processor 215. Communication interface 240 communicates with one or more remote devices, such as a clinician or patient programmer. To communicate with remote devices, communication interface 240 may include, for example, a wired network adapter, a wireless network adapter, a radio-frequency (RF) adapter, and/or a mobile telecommunications adapter.

Figure 3:
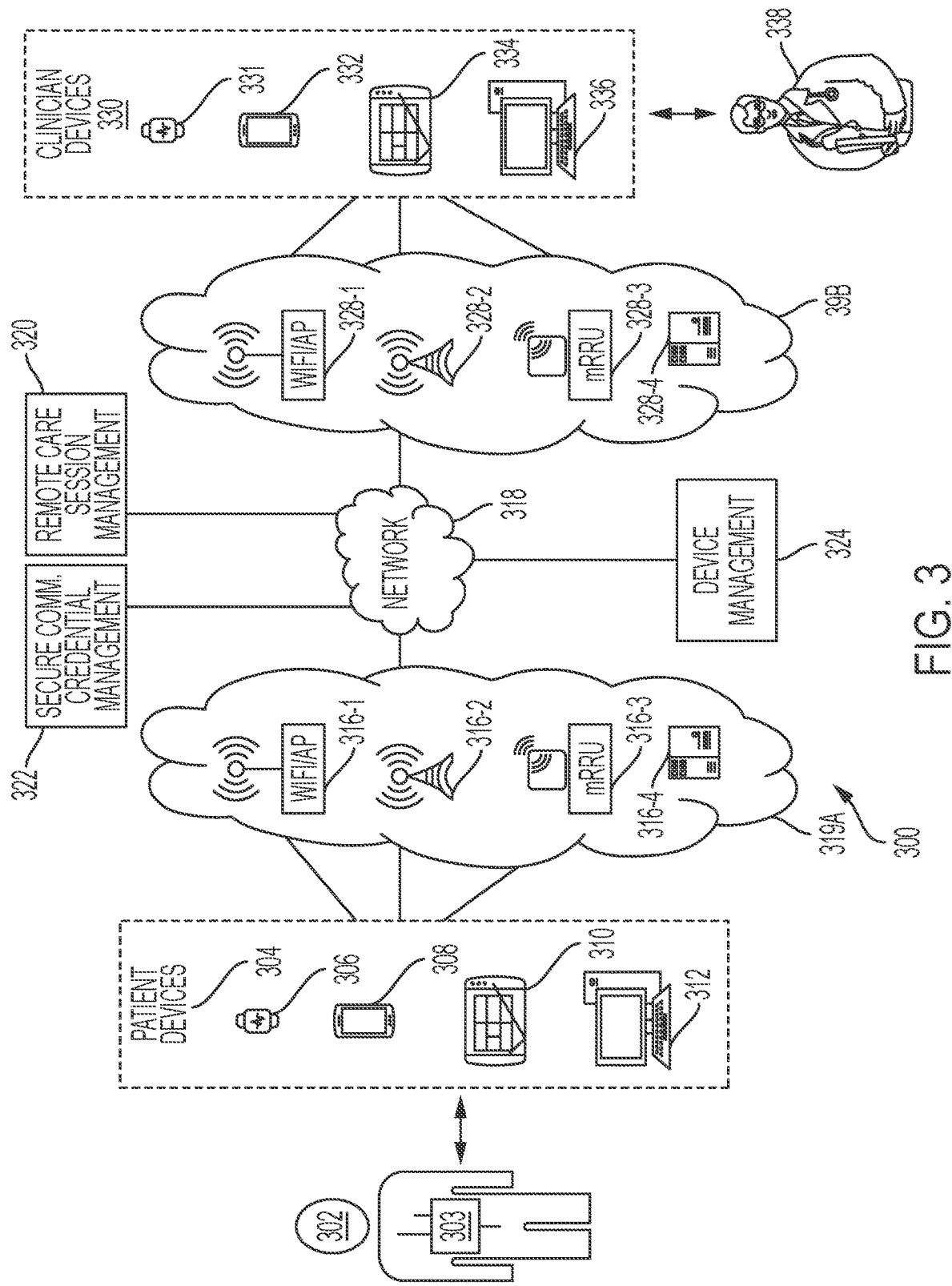
FIG. 3 depicts a network environment for remote management of patient care according to some embodiments.

FIG. 3 depicts a network environment 300 for remote management of patient care. One or more embodiments of a remote care therapy application or service may be implemented in network environment 300, as described herein. In general, "remote care therapy" may involve any care, biomedical monitoring, or therapy that may be provided by a clinician, a medical professional or a healthcare provider, and/or their respective authorized agents (including digital/virtual assistants), with respect to a patient over a communications network while the patient and the clinician/provider are not in close proximity to each other (e.g., not engaged in an in-person office visit or consultation). Accordingly, in some embodiments, a remote care therapy application may form a telemedicine or a telehealth application or service that not only allows healthcare professionals to use electronic communications to evaluate, diagnose and treat patients remotely, thereby facilitating efficiency as well as scalability, but also provides patients with relatively quick and convenient access to diversified medical expertise that may be geographically distributed over large areas or regions, via secure communications channels as described herein.

Network environment 300 may include any combination or sub-combination of a public packet-switched network infrastructure (e.g., the Internet or worldwide web, also sometimes referred to as the "cloud"), private packet-switched network infrastructures such as Intranets and enterprise networks, health service provider network infrastructures, and the like, any of which may span or involve a variety of access networks, backhaul and core networks in an end-to-end network architecture arrangement between one or more patients, e.g., patient(s) 302, and one or more authorized clinicians, healthcare professionals, or agents thereof, e.g., generally represented as caregiver(s) or clinician(s) 338.

Example patient(s) 302, each having a suitable implantable device 303, may be provided with a variety of corresponding external devices for controlling, programming, otherwise (re)configuring the functionality of respective implantable medical device(s) 303, as is known in the art. Such external devices associated with patient(s) 302 are referred to herein as patient devices 304, and may include a variety of user equipment (UE) devices, tethered or untethered, that may be configured to engage in remote care therapy sessions. By way of example, patient devices 304 may include smartphones, tablets or phablets, laptops/desktops, handheld/palmtop computers, wearable devices such as smart glasses and smart watches, personal digital assistant (PDA) devices, smart digital assistant devices, etc., any of which may operate in association with one or more virtual assistants, smart home/office appliances, smart TVs, virtual reality (VR), mixed reality (MR) or augmented reality (AR) devices, and the like, which are generally exemplified by wearable device(s) 306, smartphone(s) 308, tablet(s)/phablet(s) 310 and computer(s) 312. As such, patient devices 304 may include various types of communications circuitry or interfaces to effectuate wired or wireless communications, short-range and long-range radio frequency (RF) communications, magnetic field communications, Bluetooth communications, etc., using any combination of technologies, protocols, and the like, with external networked elements and/or respective implantable medical devices 303 corresponding to patient(s) 302.

With respect to networked communications, patient devices 304 may be configured, independently or in association with one or more digital/virtual assistants, smart home/premises appliances and/or home networks, to effectuate mobile communications using technologies such as Global System for Mobile Communications (GSM) radio access network (GRAN) technology, Enhanced Data Rates for Global System for Mobile Communications (GSM) Evolution (EDGE) network (GERAN) technology, 4G Long Term Evolution (LTE) technology, Fixed Wireless technology, 5th Generation Partnership Project (SGPP or 5G) technology, Integrated Digital Enhanced Network (IDEN) technology, WiMAX technology, various flavors of Code Division Multiple Access (CDMA) technology, heterogeneous access network technology, Universal Mobile Telecommunications System (UMTS) technology, Universal Terrestrial Radio Access Network (UTRAN) technology, All-IP Next Generation Network (NGN) technology, as well as technologies based on various flavors of IEEE 802.11 protocols (e.g., WiFi), and other access point (AP)-based technologies and microcell-based technologies such as femtocells, picocells, etc. Further, some embodiments of patient devices 104 may also include interface circuitry for effectuating network connectivity via satellite communications. Where tethered UE devices are provided as patient devices 304, networked communications may also involve broadband edge network infrastructures based on various flavors of Digital Subscriber Line (DSL) architectures and/or Data Over Cable Service Interface Specification (DOCSIS)-compliant Cable Modem Termination System (CMTS) network architectures (e.g., involving hybrid fiber-coaxial (HFC) physical connectivity). Accordingly, by way of illustration, an edge/access network portion 119A is exemplified with elements such as WiFi/AP node(s) 316-1, macro/microcell node(s) 116-2 and 116-3 (e.g., including micro remote radio units or RRUs, base stations, eNB nodes, etc.) and DSL/CMTS node(s) 316-4.

Similarly, clinicians 338 may be provided with a variety of external devices for controlling, programming, otherwise (re)configuring or providing therapy operations with respect to one or more patients 302 mediated via respective implantable medical device(s) 303, in a local therapy session and/or remote therapy session, depending on implementation and use case scenarios. External devices associated with clinicians 338, referred to herein as clinician devices 330, may include a variety of UE devices, tethered or untethered, similar to patient devices 304, which may be configured to engage in remote care therapy sessions as will be set forth in detail further below. Clinician devices 330 may therefore also include devices (which may operate in association with one or more virtual assistants, smart home/office appliances, VRAR virtual reality (VR) or augmented reality (AR) devices, and the like), generally exemplified by wearable device(s) 331, smartphone(s) 332, tablet(s)/phablet(s) 334 and computer(s) 336. Further, example clinician devices 330 may also include various types of network communications circuitry or interfaces similar to that of patient device 304, which may be configured to operate with a broad range of technologies as set forth above. Accordingly, an edge/access network portion 319B is exemplified as having elements such as WiFi/AP node(s) 328-1, macro/microcell node(s) 328-2 and 328-3 (e.g., including micro remote radio units or RRUs, base stations, eNB nodes, etc.) and DSL/CMTS node(s) 328-4. It should therefore be appreciated that edge/access network portions 319A, 319B may include all or any subset of wireless communication means, technologies and protocols for effectuating data communications with respect to an example embodiment of the systems and methods described herein.

In one arrangement, a plurality of network elements or nodes may be provided for facilitating a remote care therapy service involving one or more clinicians 338 and one or more patients 302, wherein such elements are hosted or otherwise operated by various stakeholders in a service deployment scenario depending on implementation (e.g., including one or more public clouds, private clouds, or any combination thereof). In one embodiment, a remote care session management node 320 is provided, and may be disposed as a cloud-based element coupled to network 318, that is operative in association with a secure communications credentials management node 322 and a device management node 324, to effectuate a trust-based communications overlay/tunneled infrastructure in network environment 300 whereby a clinician may advantageously engage in a remote care therapy session with a patient.

U.S. Pat. No. 10,124,177 discloses a system for conducting a remote programming session for an implantable medical device of patient where the clinician operates a clinician programmer at a site that is remote from the location of the patient. U.S. Pat. No. 10,124,177 is incorporated herein by reference.

In the embodiments described herein, implantable medical device 303 may be any suitable medical device. For example, implantable medical device may be a neurostimulation device that generates electrical pulses and delivers the pulses to nervous tissue of a patient to treat a variety of disorders.

Although implantable medical device 303 is described in the context of a neurostimulation device herein, those of skill in the art will appreciate that implantable medical device 303 may be any type of implantable medical device.

In some embodiments, patient activity data is aggregated and processed to identify performance of patient activities. For example, location data ay be obtained using wearable device 170 and/or controller device 160 to identify patient activity. For example, microlocation processing may be employed to track the patient through the patient's residence. Microlocation uses BLUETOOTH beacon devices placed at known locations to permit tracking of an individual's location with a relatively degree of precision within an indoor environment. Additionally, details regarding microlocation processing may be found in: L. B. Das et al., "Determination Of Microlocation Using the BLE Protocol, and Wireless Sensor Networks," 2018 *IEEE 3rd International Conference on Computing, Communication and Security (ICCCS)*, Kathmandu, 2018, pp. 64-69, doi: 10.1109/CCCS.2018.8586813 which is incorporated herein by reference. The microlocation processing may identify patient activity by identify time spend in specific areas. For example, a meal may be identified by the patient spending time within the patient's dining area.

In some embodiments, other protocols are employed to identify activities of a patient. For example, global positioning system (GPS) circuitry may obtain location data and processed. The GPS data may identify the patient as being at the patient's work location and thereby identify the patient activity as "WORKING" at such times. Also, the GPS data may identify the user as moving relatively rapidly thereby correlating the patient activity to "COMMUTING" or "DRIVING" as the GPS data indicates. Methods for correlating activities of individuals to locations are known in the art and described in, for example, the article Location-based Activity Recognition by Lin Liao, Dieter Fox, and Henry Kautz in Neural Information Processing Systems (NIPS), 2005, which is incorporated herein by reference.

In some embodiments, activity monitoring functionality of wearable device 170 may be employed to identify patient activity. For example, the sleep monitoring functionality may identify times of sleep by a patient from movement data, heart rate data, and other relevant physiological data. Examples of sleep stage classification are described in U.S. Pat. No. 10,786,676 and U.S. Patent App. Pub. No. 20050043652 which are incorporated herein by reference.

The identification of patient activities may use the techniques described in U.S. Pat. No. 10,314,550 as an example.

Figure 4:
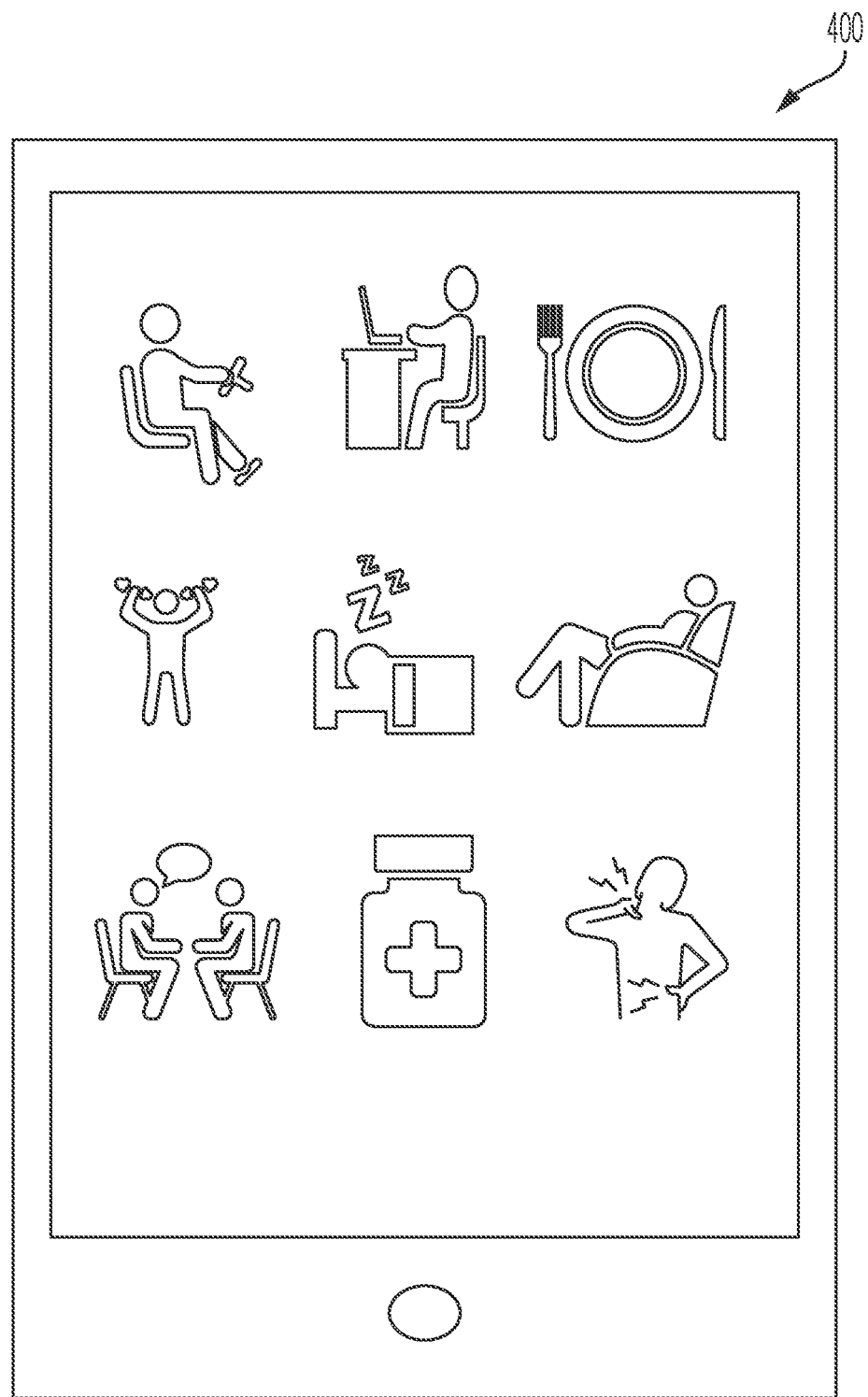
FIG. 4 depicts a user interface that provides a number of icons that represent activities of the patient according to some embodiments.

In some embodiments, patient activity data may be directly identified by the patient using wearable device 170 and/or controller device 160. As shown in FIG. 4, user interface 400 provides a number of icons that represent activities of the patient. User interface 400 may be provided by external controller 160. Similar icons could be provided by wearable device 170 although the presentation could be provided in a different arrangement to accommodate to the typical smaller screen size of wearable devices. The icons shown in FIG. 4 correspond to driving, working, eating, exercising, sleeping, resting, talking, and taking medication. Any number of other icons could be provided to represent other user activities. In some embodiments, the user and/or the clinician may select from a number of predefined activities for use on a specific user's device as deemed most relevant to the patient and/or the clinician. Additionally, the icons include a "PAIN" symptom icon that permits the user to provide an indication of the amount of pain that the patient is currently experiencing at any given time. If the stimulation system is intended to treat a condition other than chronic pain, the symptom icon may reflect other conditions such as tremor, difficulty moving, dyskinesia, or other conditions. The icons available for selection by a user may be customizable according to some embodiments. For example, the patient or the patient's clinician may select icons for use by the patient from a larger set of icons depending upon relevance to the patient. Predefined sets of a plurality of icons may also be defined for selection by the patient and/or the patient's clinician for use by patient according to patient disorder (e.g., chronic pain, movement disorder, and/or other neurological disorders) and patient relevant data (e.g., age, gender, health condition, etc.).

Figure 5:
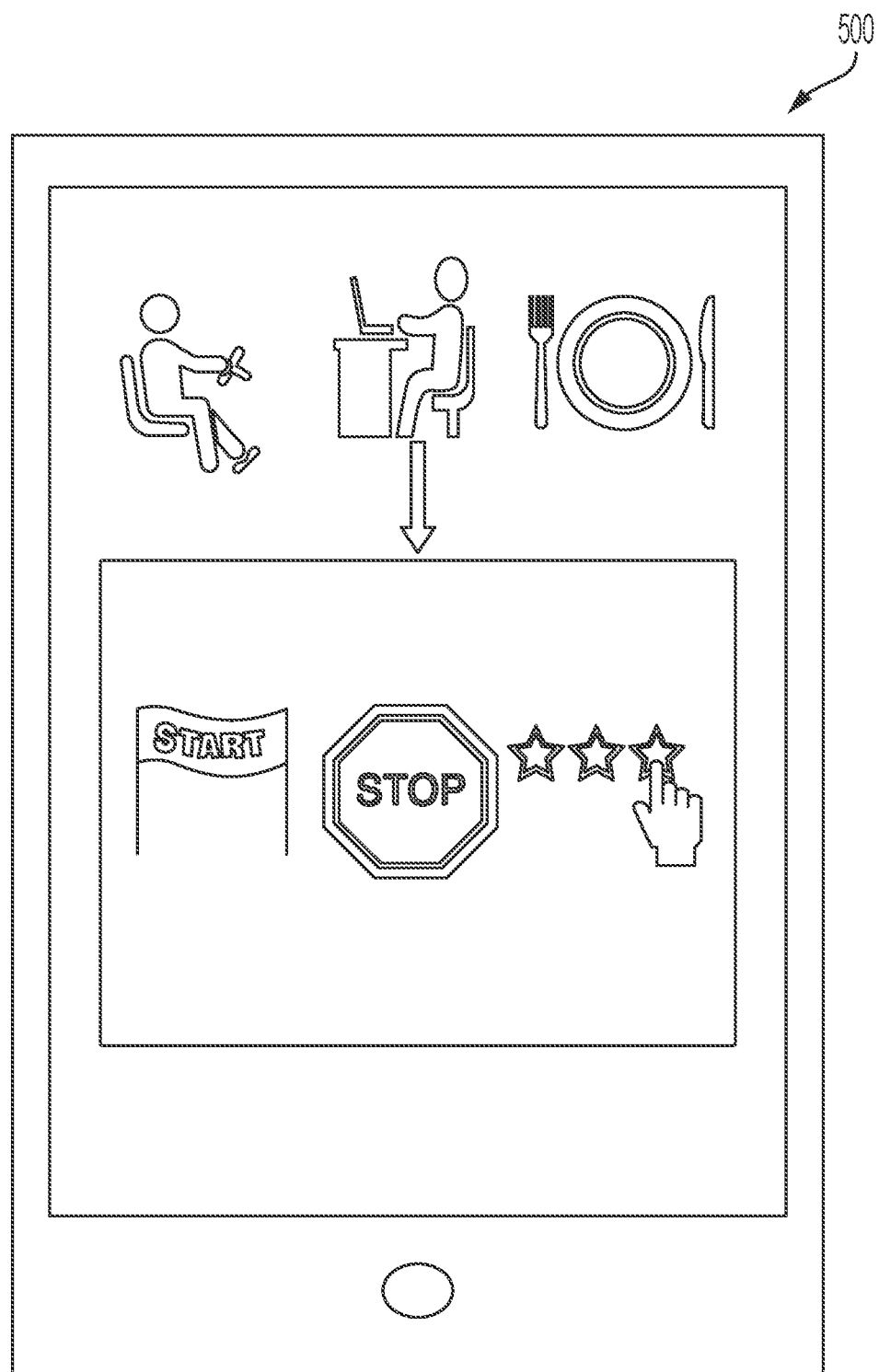
FIG. 5 depicts a user interface for receiving additional patient data according to some embodiments.

When the user begins, ends, or otherwise engages in an activity, the user may select one of the icons. The user selection is recorded in an activity log. Also, as shown in FIG. 5, user interface 500 may be provided that presents additional options for selection by the user upon selection of one of the activity icons. The user may select an icon to indicate that the user has just begun the activity ("start"), or has completed the activity ("stop"). Also, the user may provide an indication of the relatively quality, ease, difficulty, etc. of the activity for the patient by selecting the "RATING" icon. For example, if the user is experiencing difficulty completing the patient's work activity, the patient may select a lower rating or score for the activity.

The various user indications of activity and other user inputs are logged and communicated to a remote care management system by external controller device 160 and/or wearable device 170. The remote care management system stores the user activity data. Also, external controller device 160 and/or wearable device 170 may communicate user activity data obtained by these devices using sensors or other functionality of the devices.

Figure 6:
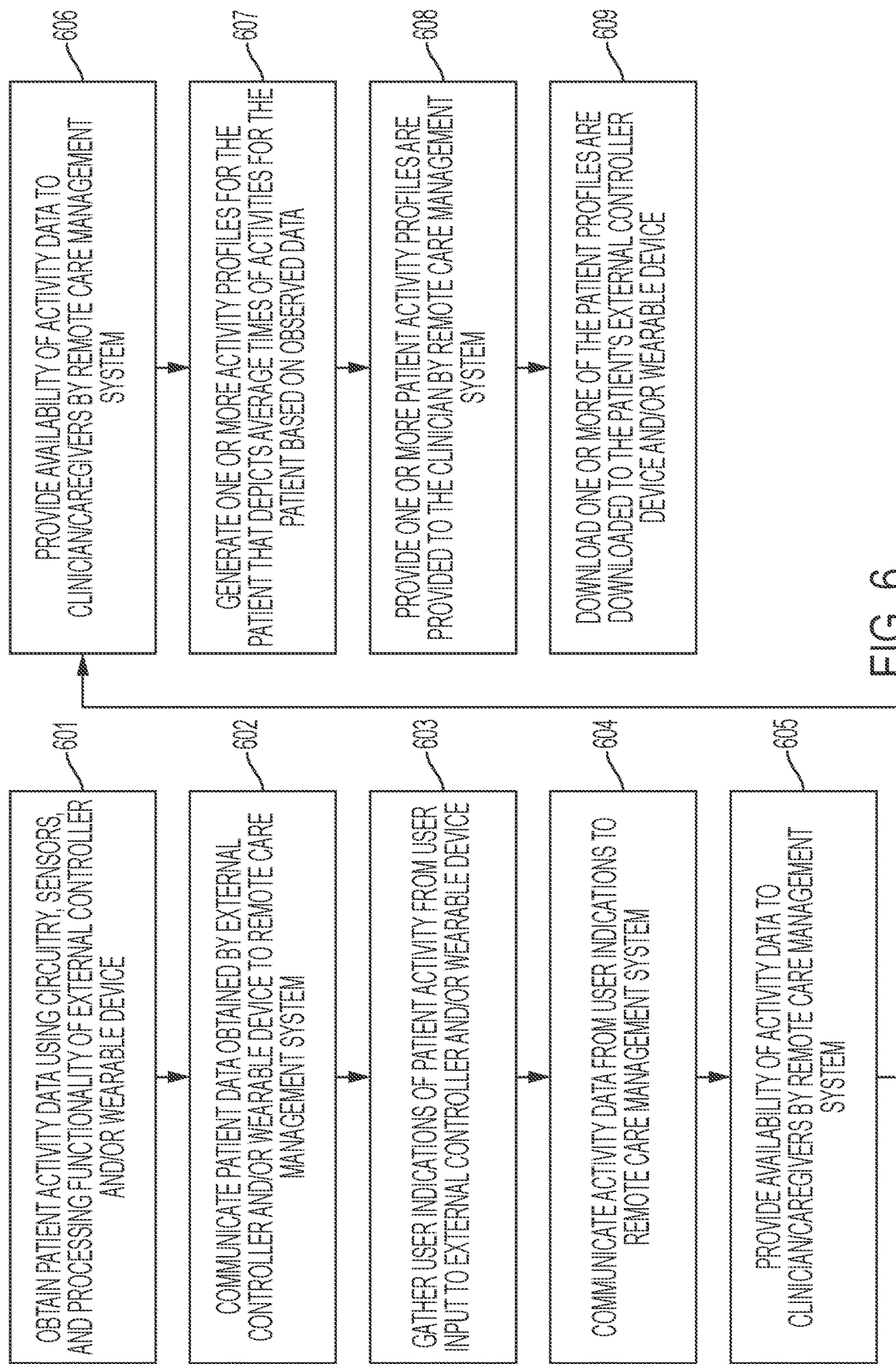
FIG. 6 depicts a flowchart for aggregating and processing patient activity data to manage patient care according to some embodiments.

FIG. 6 depicts a flowchart for aggregating and processing patient activity data to manage patient care according to some embodiments. In step 601, patient activity is obtained by external controller device 160 and/or wearable device 170 using circuitry, sensors, and processing functionality of these devices. The patient activity data may include movement data, sleep data heart rate data, electrocardiogram data, body temperature data, blood saturation data, and/or any other relevant data available from these devices. Additionally, other data from other medical devices may be gathered for use in accordance with some embodiments. For example, the glucose monitoring devices generate data related to the amount of glucose in the patient's blood stream. Glucose monitoring devices include the FREESTYLE LIBRE glucose monitor device available from ABBOTT. In 602, the patient data is communicated to a remote care management system where it is stored for a given patient.

In 603, user indications of patient activity are gathered by external controller device 160 and/or wearable device 170. The patient data may include indications of levels of difficulty or ease associated with specific activity, start times, stop times, pain or other symptom levels, and/or any other relevant data. In 604, the patient inputted data is communicated to a remote care management system where it is stored for a given patient.

In 605, the data is made available to the patient's clinician(s) and/or caretaker(s). The clinicians may review the data to make decisions to modify the patient's neurostimulation therapy or provide other suitable medical or health care for the patient. The data may be made available by providing reports of the patient activity in graphical format when the clinician accesses patient data through a session with the remote care management system.

In 606, the remote care system generates one or more activity profiles for the patient that depicts average times of activities for the patient based on observed data. The average times may also be determined such that a separate profile is developed for each day of the week.

In 607, one or more patient activity profiles are provided to the clinician to make decisions to modify the patient's neurostimulation therapy or provide other suitable medical or health care for the patient. The data may be made available by providing reports of the patient profile(s) in graphical format when the clinician accesses patient data through a session with the remote care management system.

In 608, one or more of the patient profiles are downloaded to the patient's external controller device 160 and/or wearable device 170 according to some embodiments. In some embodiments, the patient's neurostimulation therapy may be controlled based on patient activities and/or the patient's activity profile.

Figure 7:
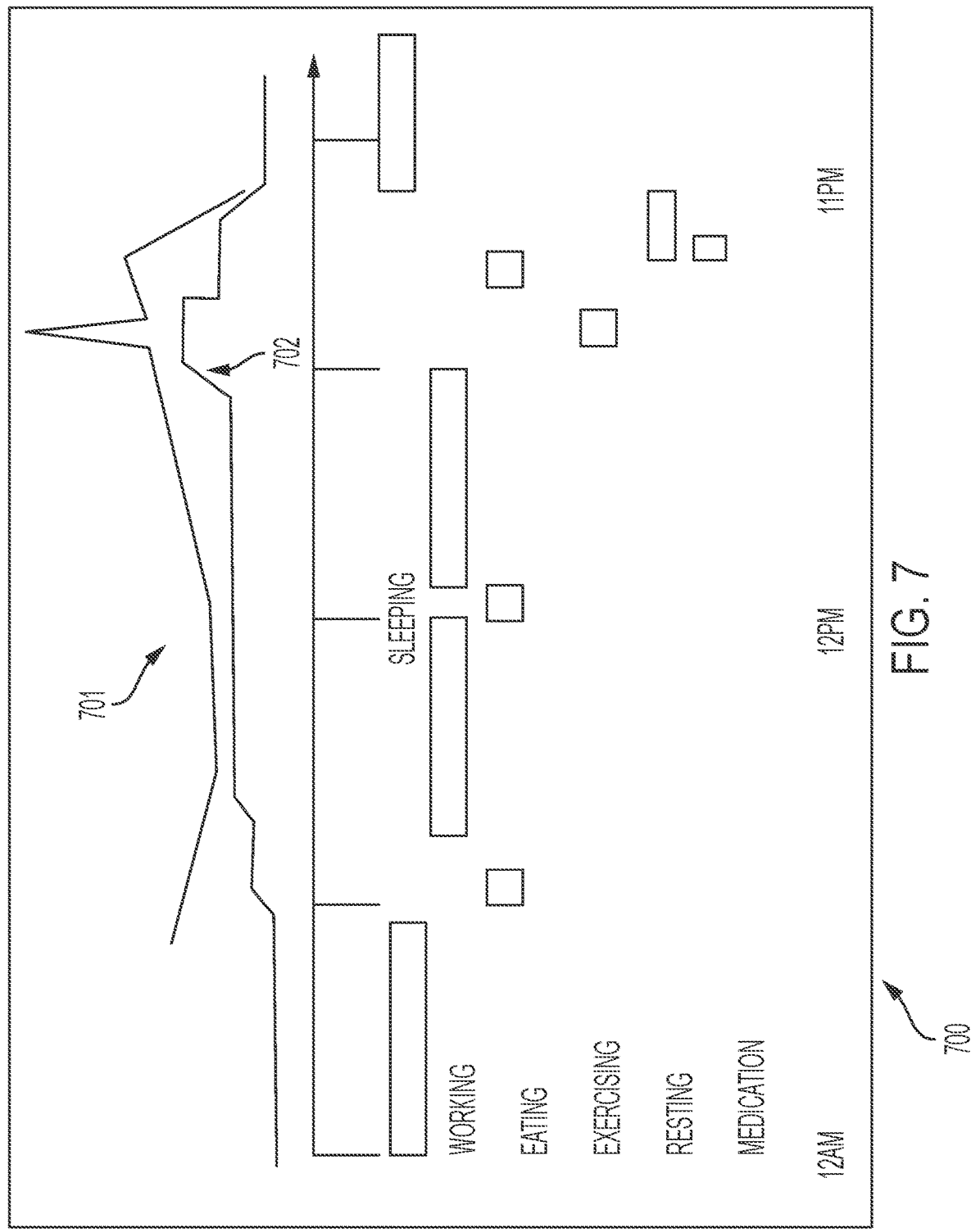
FIG. 7 depicts a patient activity graph according to one representative embodiment.

FIG. 7 depicts patient activity graph 700 according to one representative embodiment. The patient activity graph 700 may represent the actual activities detected for a patient on a given day. Alternatively, the graph may represent activities for a statistically average day for a given patient. Graph 700 shown the actual times or expected times for each representative activity. Also, graph 700 depicts symptom severity representation 701. Symptom severity representation 701 may, for example, represent an interpolated graph of the pain report pain scores through the day. The clinician may use the representation of the patient's pain to control the neurostimulation provided to the patient. Also, the clinician may identify relationships between patient pain and specific activities.

In some embodiments, the clinician may select a point in time along graph 700 and view any patient reported activity and/or any physiological or other data captured by wearable device 170 and/or external controller 160. For example, the clinician may review patient sleep quality to identify relationships between the patient's condition and other external factors or activities. The clinician may review heart rate or other cardiac activity data, body temperature data, blood glucose levels, blood oxygen levels, or any other measured physiological data according to some embodiments. In some embodiments, the clinician may select an option to display physiological data overlaying the activities of the patient. For example, as depicted in FIG. 7, graph 702 represents a time-window averaged heart rate of the patient at respective times. Any of physiological or other signals described herein could be displayed in a similar manner at the option of the clinician when conducting a session with the remote care management system to review patient activity data. As previously discussed, graph 702 could represent actual measurement data for a specific day or average physiological data depending upon whether the clinician wishes to review data for a specific date or review the patient's profile.

Figure 8:
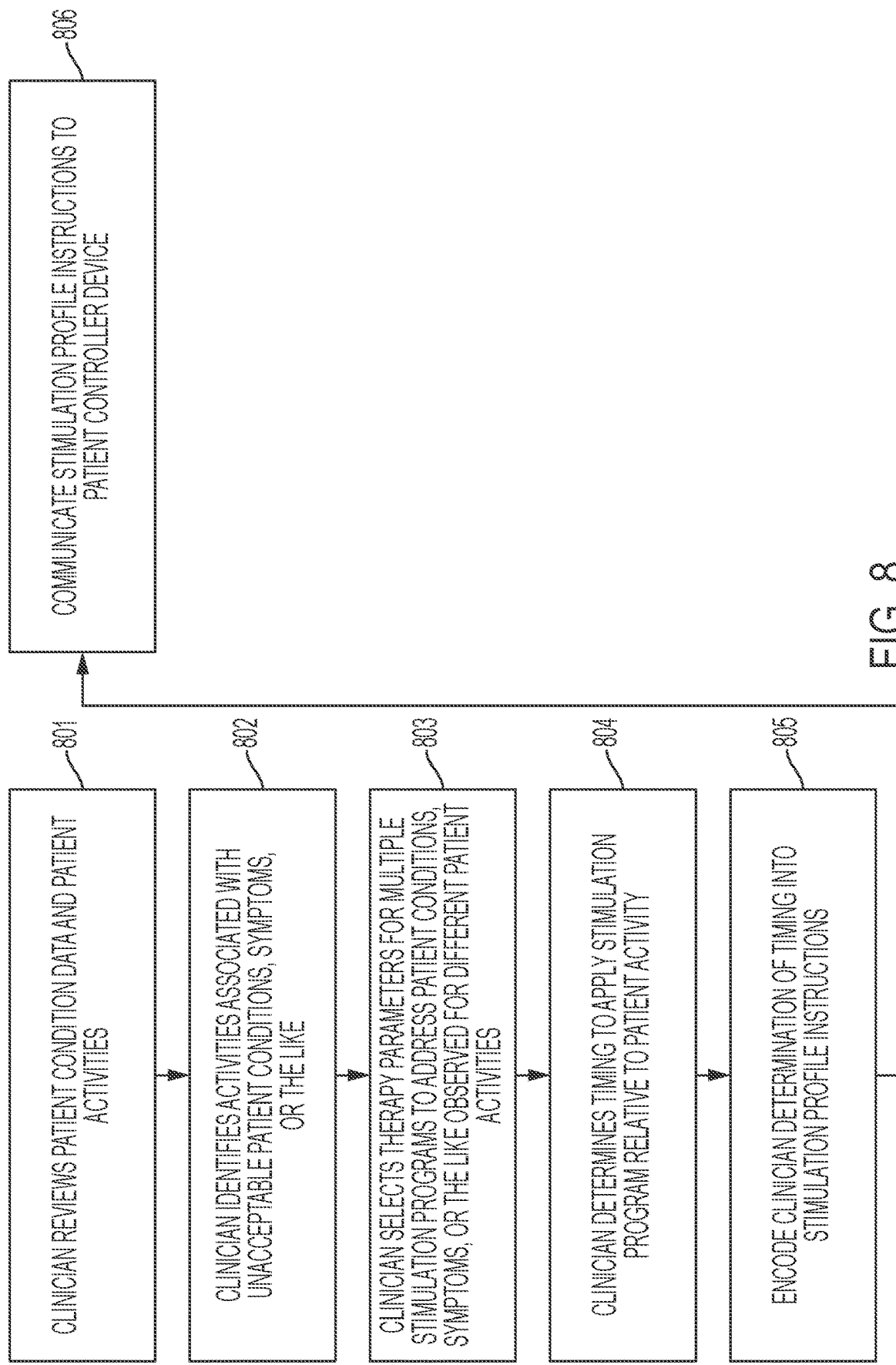
FIG. 8 depicts a flowchart of activities and operations to employ patient activity data to develop a stimulation therapy with stimulation parameters selected according to different patient activities.

FIG. 8 depicts a flowchart of activities and operations to employ patient activity data to develop a stimulation therapy with stimulation parameters selected according to different patient activities. In 801, a clinician reviews patient condition data and patient activities. In 802, the clinician identifies activities associated with unacceptable patient conditions, symptoms, or the like. The patient condition data may include objectively measured data such as data related to patient movement (movement disorder symptoms), cardiac activity, EMG data, respiration data, blood glucose data, and/or any other sensed data. The patient condition data may include subjectively captured data such as patient indicated data from the patient's controller device. The subjective data may include pain levels, difficulty performing tasks, psychological data (e.g., affect levels, anxiety levels, etc.), or any other relevant patient reported information.

In 803, clinician selects therapy parameters for multiple stimulation programs to address patient conditions, symptoms, or the like observed for different patient activities. For example, the clinician may observe that the patient experiences higher pain levels while working or walking as examples. The clinician may define an additional stimulation program beyond a default stimulation program to address the higher level of pain during such activities. As another example, the clinician may observe that the patient experiences some level of difficulty swallowing when a stimulation program adapted to achieve optimally motor disorder symptom suppression occurs. The clinician may define an additional stimulation program to reduce this side-effect while still achieve an acceptable but lower degree of motor disorder symptom suppression for use when the patient is eating a meal.

In some embodiments, the stimulation pattern applied to the patient via different stimulation programs may differ. For example, "coordinated reset" stimulation and tonic stimulation have both been applied for Parkinson's Disease. Although coordinated reset stimulation is suggested to have some clinical benefits to restore a patient's neural activity to a natural non-synchronized state from a pathological synchronized state, tonic stimulation may have a more immediate impact on certain movement disorder symptoms than coordinated reset stimulation. A clinician may conclude that tonic stimulation in DBS may be beneficial for a patient for a limited time while the patient is engaged in a specific activity or is experiencing one or more specific symptoms. The clinician may define different stimulation programs using a coordinated reset stimulation pattern and a tonic stimulation patterns and associate such stimulation programs with different patient activities and/or patient conditions.

In 804, the clinician determines timing to apply stimulation program relative to patient activity. For example, the clinician may determine that a patient will receive the most benefit if a given stimulation program begins before the patient begins an expected activity. Alternatively, the clinician may conclude that a specific stimulation program should only be used when the patient is detected engaging in the specific activity. In yet other cases, the clinician may observe that a specific activity induces a patient condition (pain level) after some lag time. For example, a patient may exercise and not experience much difference in their subjective condition while actually exercising but may experience increased pain some time after halting the exercise. The clinician may conclude that a stimulation program to address the increase in the patient's pain level is appropriate beginning thirty minutes after completion of the given activity. As yet another example, the clinician may select different stimulation programs to be applied relative to the timing of the ingestion of medication or pharmaceutical compounds.

In some embodiments, other timing parameters defined by the clinician may control the relative amount of application of one or more of the stimulation programs. For example, tonic stimulation (whether for DBS, SCS, or other neurostimulation therapies) may be shown to develop habituation in patients. It posited that habituation may occur whether low frequency (below 100 Hz) or high frequency (e.g., 500 Hz-10,000 Hz or higher) or whether stimulation is applied with or without paresthesia. Although habituation has been observed for tonic stimulation, tonic stimulation may produce superior reduction in neurological symptoms (movement disorder symptoms as an examples) for patients in specific circumstances and, perhaps, for short periods of time. For example, a patient's perception of chronic pain may involve a temporary increased level of pain based on a temporary patient condition (possibly induced by a specific activity). In such cases, it may be preferred to switch to tonic stimulation from other stimulation pattern (e.g., burst stimulation, high-frequency no-paresthesia stimulation, coordinated reset stimulation) for a limited period of time when pain is induced by a specific stimuli (although the reverse may also be true where switching from tonic to non-tonic stimulation will produce an improved patient response in some cases). In any event, the switch between stimulation patterns may be limited by the clinician to a defined time limit. The patient response to different types of stimulation may differ between patients and differ according to different activities. The ability to switch stimulation types according to patient and activity specific situations may improve patient outcomes.

In some embodiments, the clinician may define one or more preferred percentage parameters (e.g., 25% of the time in a day) that one or more specific stimulation patterns are applied. The clinician could also define the relative percentages of time that two or more different stimulation patterns are applied (e.g., 75% of the time for burst stimulation and coordinated reset stimulation and 25% of the time for tonic stimulation). The clinician may limit the number of hours of tonic stimulation to a specific time limit (e.g., four hours in a day). With such limits, the clinician may also specific stimulation patterns for specific activities (e.g., coordinated reset stimulation is preferred while the patient is sleeping or resting).

In 805, the clinician's determination of appropriate timing for the stimulation programs are encoded into stimulation profile instructions. In 806, the stimulation profile instructions are communicated to the patient's controller device to control the patient's neurostimulation (which may include automated scheduling and balancing of patterns according to observed patient activity).

Figure 9:
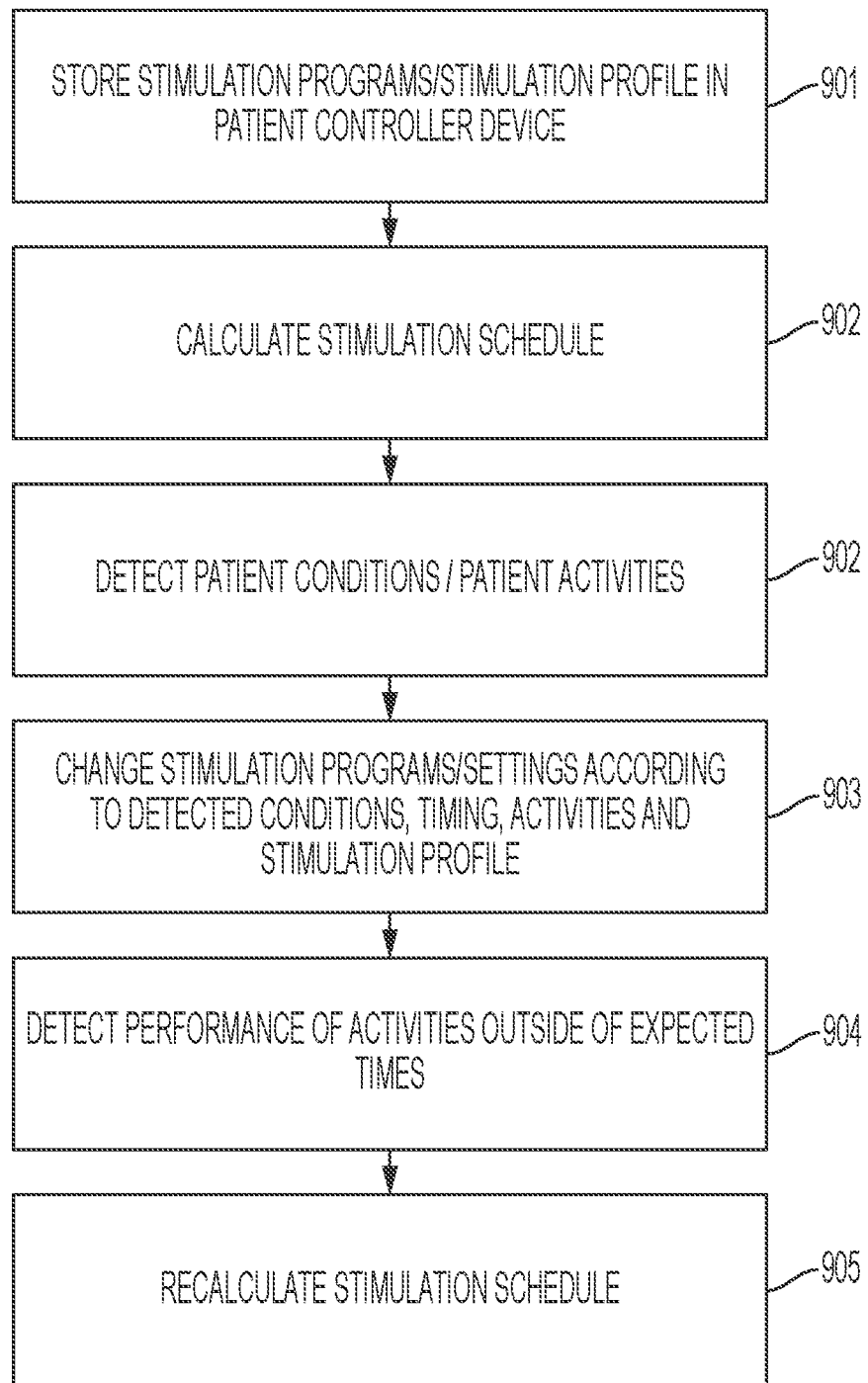
FIG. 9 depicts a flowchart of activities and operations to create a stimulation schedule based on expected user activities according to some embodiments.

FIG. 9 depicts a flowchart of activities and operations to create a stimulation schedule based on expected user activities according to some embodiments. In 901, the stimulation programs and stimulation profile are stored in patient controller device. The patient controller device may communicate directly with a clinician programmer to receive the relevant data. Alternatively, the patient controller device may receive the relevant data during one or more remote programming sessions.

In 902, stimulation schedule is calculated. The calculation of the stimulation schedule may occur using software operations on the patient controller device. In alternative embodiments, the initial stimulation schedule may be calculated by software on a server of the remote care management system. The calculation of the stimulation schedule may begin by referring to an expected schedule of patient activities that is generated by monitoring patient activities over a period of time. In a first pass, the calculation of the stimulation schedule applies timing rules that uniquely require specific time periods for specific stimulation programs. For example, the clinician may have defined a timing rule for a specific stimulation program to be applied while the patient is sleeping. The times that are not uniquely defined by such clinician defined rules are left empty. The remaining times may be filled with selections from the available stimulation programs. The selection may limit application of certain stimulation programs according to total time limits or percentage of time limits. With these constraints applied, various scheduling algorithms may be applied such as random scheduling, shortest or longest time allocation scheduling (where the stimulation program with the shortest or longest allocated time is prioritized), priority scheduling (where specific stimulation programs are provided a priority weight), round robin scheduling, or any other suitable scheduling algorithm.

In 903, the patient controller device changes stimulation programs/settings according to detected conditions, timing, activities and stimulation profile. That is, the patient controller receives data from sensors, receive user input for activities and patient conditions, receives location data indicative of the patient's location and determines the patient's current activity and condition. The patient controller device switches between stimulation programs based on this data. When the patient controller device detects a change in activity (e.g., indirectly through sensor data or directly through user input or by merely time of day based on the patient's activity profile), the patient controller device communicates relevant data to the implantable pulse generator of the patient to apply a different stimulation program and/or stimulation parameters. In some embodiments, the patient controller may prompt the user to authorize the change before actually communicating the stimulation modification signal to the patient's implantable pulse generator. The patient controller device communicates the relevant data to the patient's implantable pulse generator using wireless communication such as low energy BLUETOOTH™ communications to apply the change in stimulation.

In 904, the patient controller device detects performance of activities outside of expected times. In 905, the stimulation schedule is recalculated by the patient's external controller device (or by a remote server) based on the respective activity outside of an expected time.

Figure 10:
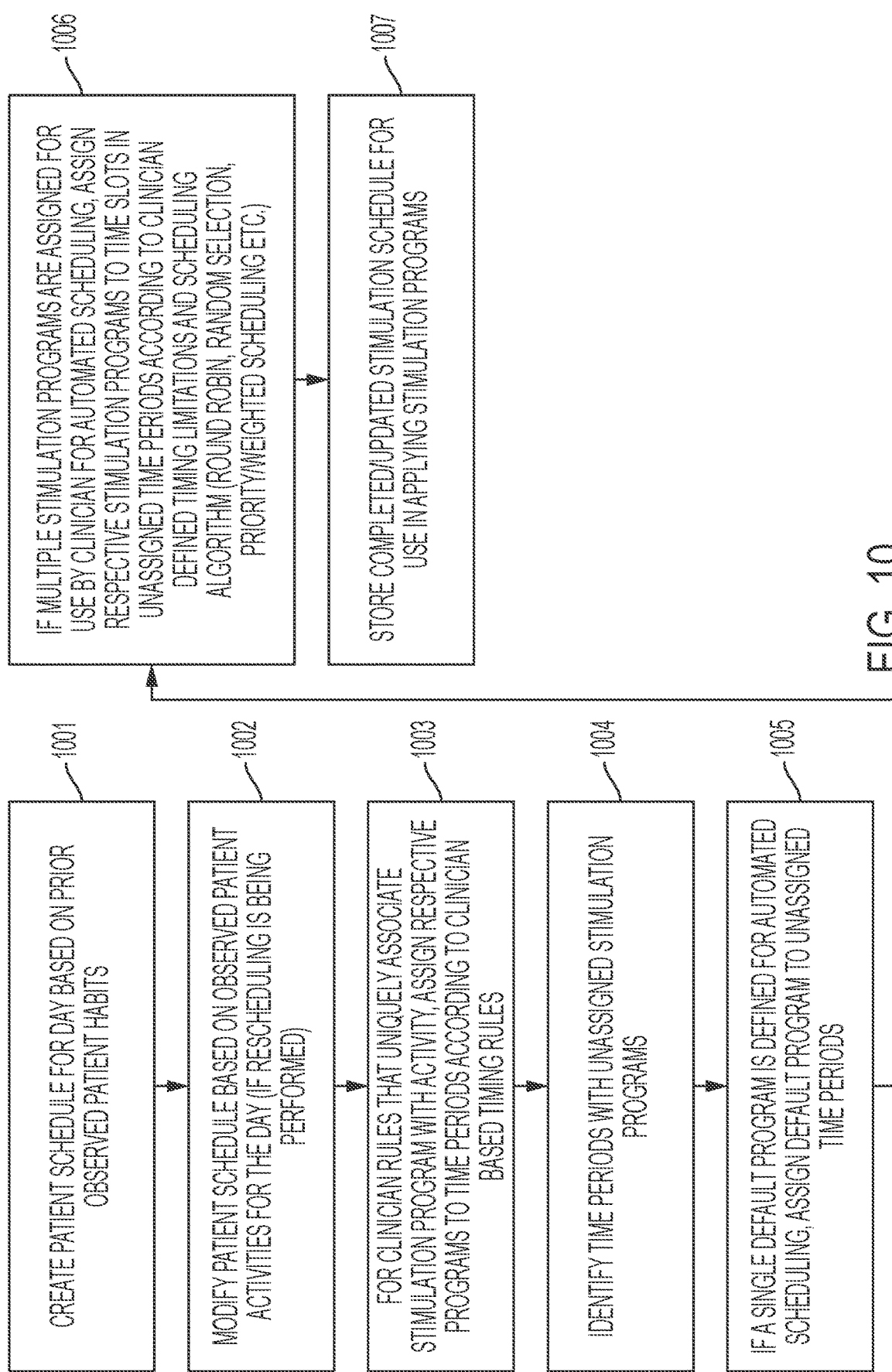
FIG. 10 depicts a series of operations that may be performed by a patient controller device or a remote server to control neurostimulation applied to a patient according to some embodiments.

FIG. 10 depicts a series of operations that may be performed by a patient controller device or a remote server to control neurostimulation applied to a patient according to some embodiments. In 1001, a patient schedule is created for a given day based on previously observed patient habits. The previously observed habits may be identified using sensors and activity detecting algorithms as discussed in this application. In 1002, the created patient schedule is modified based on observed patient activities for the day (if rescheduling is being performed). For example, the patient may leave for work at an earlier time, have lunch at a later time, exercise at a different time, etc. The patient schedule is modified to reflect actual, observed performance of activities as the activities are detected by the patient's external controller device or other device.

For clinician rules that uniquely associate stimulation program with activity, respective programs are assigned to time periods according to clinician based timing rules (1003). For example, the programming clinician may assign a specific stimulation program for rest/sleep periods of the patient and another specific stimulation program for activities requiring substantial patient movement (e.g., work or exercise). The stimulation schedule is updated to assign such stimulation programs to time periods for the respective activities.

The clinician may not specifically assign stimulation programs to every possible activity of the patient. Accordingly, some time periods will not have a specific program assigned at this initial stage. In 1004, time periods with unassigned stimulation programs are identified. The clinician may assign one specific default stimulation program for general use. Accordingly, in 1005, if a single default program is defined for automated scheduling, assign default program to unassigned time periods Alternatively, the clinician may identify multiple suitable programs for the patient which may possibly have different benefits or effects. If multiple stimulation programs are assigned for use by clinician for automated scheduling, respective stimulation programs are assigned (1006) to time slots in unassigned time periods according to clinician defined timing limitations and scheduling algorithm (round robin, random selection, priority/weighted scheduling etc.). In some embodiments, a balancing of stimulation programs is applied using the scheduling algorithm. For example, the patient's clinician may specify that coordinated reset should be applied for a specific percentage of time and tonic stimulation should be applied another percentage of time. Alternatively, the clinician may specify that burst stimulation should be applied for a percentage of time and high frequency tonic stimulation for another percentage of time. The scheduling algorithm may assign these stimulation programs to the unassigned time periods such that the overall percentages are obtained for the given day.

In 1007, the completed or updated stimulation schedule is stored for use in applying stimulation programs.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

The invention claimed is:

1. A method of providing neurostimulation to a patient, comprising:
   monitoring activities of the patient using at least one external device, wherein the monitoring comprises obtaining data pertaining to physiological signals of the patient using a wearable device;
   communicating patient activity data to a remote care management system, wherein the remote care management system determines an activity profile for the patient that represents expected times when the patient will engage in a plurality of different activities of the patient;
   storing a plurality of different stimulation programs for use by a neurostimulation system of the patient, wherein each stimulation program is adapted to provide a different stimulation effect on the patient; and
   controlling an implantable pulse generator of the neurostimulation system to generate electrical pulses according to ones of the plurality of different stimulation programs with different stimulation effects for application to neural tissue of the patient according to times defined by at least the activity profile of the patient, wherein the controlling comprises: retrieving a stimulation scheduling parameter that defines a percentage or length of time for scheduling an identified stimulation program and dynamically adjusting scheduling of the identified stimulation program based on detected activities of the patient subject to scheduling compliance with the stimulation scheduling parameter.

2. The method of claim 1 wherein the monitoring comprises repetitively detecting a location of the patient using location determining circuitry of the external device.

3. The method of claim 2 wherein the location determining circuitry comprises at least one set of circuitry from the list consisting of: cellular communication circuitry, WiFi circuitry, and Bluetooth circuitry.

4. The method of claim 2 wherein the monitoring comprises detecting an amount of time spent at an identified location.

5. The method of claim 2 wherein the monitoring comprises detecting signals from one or more wireless beacon devices to perform microlocation processing.

6. The method of claim 1 wherein the remote care management system performs an averaging calculation of observed times for patient activities of the activity profile.

7. The method of claim 6 wherein the remote care management system calculates average start times of respective activities for the activity profile.

8. The method of claim 6 wherein the remote care management system calculates average end times of respective activities for the activity profile.

9. The method of claim 1 wherein the remote care management system applies a calculation of frequency of performance of activities to determine the activity profile.

10. The method of claim 1 wherein the remote care management system applies an averaging calculation to determine average duration of activities for the activity profile.

11. The method of claim 1 wherein the different stimulation programs comprise different stimulation amplitude levels for application of electrical pulses to the patient.

12. The method of claim 1 wherein the different stimulation programs apply electrical pulses at different frequencies.

13. The method of claim 1 wherein the different stimulation programs apply electrical pulses to different neural targets.

14. The method of claim 1 wherein the different stimulation programs apply electrical pulses using different stimulation patterns.

15. The method of claim 1 wherein the different stimulation programs cause different side effects for the patient.

16. The method of claim 1 wherein at least one of the different stimulation programs is adapted to modify blood flow to a region of the patient's body.

17. The method of claim 1 wherein at least one of the different stimulation programs is adapted to modify cardiac activity of the patient.

18. The method of claim 1 wherein at least one of the different stimulation programs is adapted to treat pain of the patient.

19. The method of claim 1 wherein the plurality of different stimulation programs treat a motor disorder of the patient.

* * * * *